(12) United States Patent
Patton et al.

(10) Patent No.: US 6,232,508 B1
(45) Date of Patent: May 15, 2001

(54) PROCESS FOR MANUFACTURING ETHER AND HIGH PURITY BUTENE-1

(75) Inventors: Gary R. Patton; Robert O. Dunn, both of Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 08/598,617

(22) Filed: Feb. 12, 1996

(51) Int. Cl.$^7$ .................................................. C07C 43/00
(52) U.S. Cl. ........................... 568/697; 568/698; 568/699
(58) Field of Search .................... 568/697, 698, 568/699

(56) References Cited

U.S. PATENT DOCUMENTS

| | | | |
|---|---|---|---|
| 3,979,461 | 9/1976 | Ancillotti et al. | 260/614 A |
| 4,546,206 | 10/1985 | Neier et al. | 568/697 |
| 4,558,168 | * 12/1985 | Gussow et al. | 585/324 |
| 5,237,109 | 8/1993 | Patton et al. | 568/697 |
| 5,338,889 | * 8/1994 | Vora et al. | 568/697 |

OTHER PUBLICATIONS

Encyclopedia of Chemical Processing and Design, vol. 30, 1989, pp. 82–86, "Methyl Tertiary Butyl Ether".

* cited by examiner

*Primary Examiner*—Dwayne C. Jones
(74) *Attorney, Agent, or Firm*—Charles W. Stewart; A. W. Umphlett

(57) ABSTRACT

A process for the manufacture of ether from a feedstock containing isoolefins and linear olefins. The process is one which has a high conversion of isoolefins thereby permitting the separation of linear olefins without the associated difficulty in separating isomers.

4 Claims, 1 Drawing Sheet

PROCESS FOR MANUFACTURING ETHER AND HIGH PURITY BUTENE-1

Figure 1:
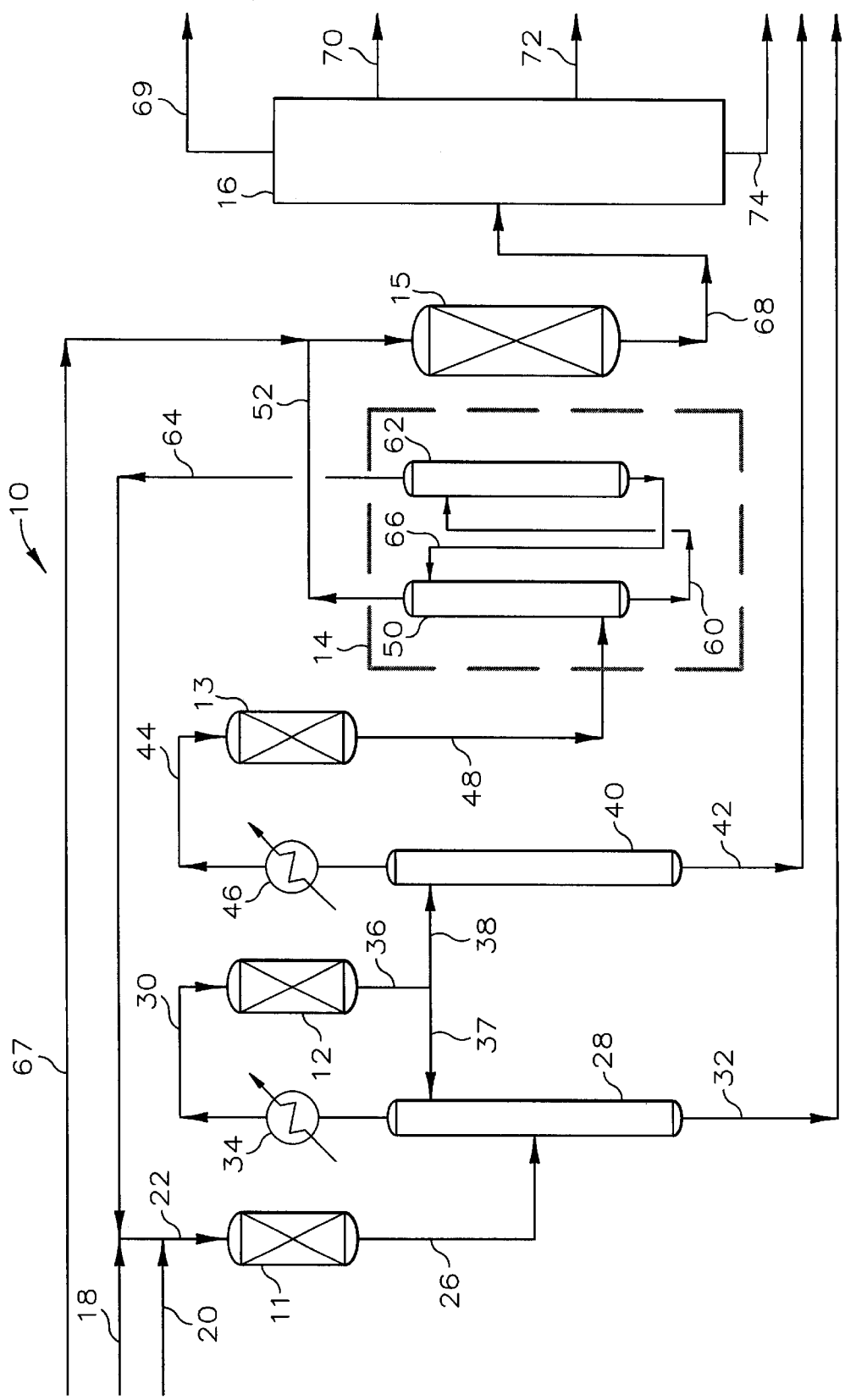

This invention relates to the production of alkyl tertiary ether compounds and a high purity butene-1 product from a mixed hydrocarbon feedstock.

It is known that alkyl tertiary alkyl ether compounds can be prepared by reacting primary or secondary alcohols with olefin compounds having a double bond on a tertiary carbon atom in the presence of an acidic ionic exchange resin catalyst. The particularly more common etherification reactions are those that involve reacting methanol with either isobutene or isoamylenes to form respectively methyl tertiary butyl ether (MTBE) and methyl tertiary amyl ether (TAME). Other etherification reactions include the reaction of ethanol with either isobutene or isoamylenes to form respectively ethyl tertiary butyl ether and tertiary amyl ethyl ether. These tertiary alkyl ether compounds are particularly useful as octane improvers for liquid fuels, especially gasoline. Also, because of the low vapor pressure of these compounds, they are particularly useful for reducing the vapor pressure of gasoline. Recent federal government regulations have resulted in the requirement that motor gasoline be reformulated to include greater concentration levels of oxygenate compounds of which tertiary alkyl ether compounds have been found to be especially suitable for assisting in compliance with these new federal regulations.

While processes for the production of high octane tertiary alkyl ethers have been known in the art, there still remains various problems with the known processes that have heretofore not been resolved by those skilled in the art. In particular, because standard etherification reactions are equilibrium type reactions, most etherification processes do not provide economical means for obtaining high olefin conversions without incurring high energy and capital costs to obtain such high olefin conversions.

In the production of tertiary alkyl ethers, a feedstock will often be a mixture of olefins including linear olefins as well as tertiary olefins. The linear olefins are generally nonreactive in an etherification reaction zone and will pass through the reaction zone without change. There can also be diolefins, such as 1,3-butadiene, present in an etherification reaction zone feed which will pass with the reactor effluent relatively unreacted. It has been found that due to the nonreactivity of linear olefins and, in particular, butene-1, an etherification reaction can be used to convert tertiary olefins of a feedstream containing isobutene and butene-1 to ether, which is relatively easily separated from butene-1, thereby permitting a reduced cost of production of high purity butene-1. In order to produce a high purity butene-1 product having a low concentration of isobutene, a high conversion etherification process may be used to assist in providing the high purity butene- I product. The 1,3-butadiene may be removed from the butene-1 product by a hydroisomerization reaction.

It is therefore an object of this invention to provide an etherification process that produces tertiary alkyl ethers at high olefin conversion rates and low operating capital costs.

Another object of the invention is to provide a process for producing a high purity butene-1 product having a low concentration of isobutene from a feedstock containing a mixture of butenes.

Other objects, aspects and features of the present invention will be evident from the following detailed description of the invention, the claims and the drawing in which:

FIG. 1 is a schematic process flow diagram illustrating one preferred embodiment of the invention.

The inventive process includes multiple etherification reaction zones, an alcohol recovery section, a hydroisomerization reaction zone, and a product separation system. Each of the etherification reaction zones uses a reactor vessel to define a reaction zone containing therein a suitable etherification catalyst for promoting or catalyzing an etherification reaction between reactive tertiary olefin compounds and primary or secondary alcohols. The hydroisomerization reaction zone also utilizes a reactor vessel to define a hydroisomerization reaction zone containing therein a hydroisomerization catalyst suitable for hydrogenating 1,3-butadiene to butene-1.

A feedstream comprising a tertiary olefin and a primary alcohol is charged or fed to a first etherification reaction zone wherein it is contacted with an etherification catalyst under suitable reaction conditions for promoting the reaction of the tertiary olefins and alcohols contained in the feedstream to produce a first etherification reactor effluent.

In many cases, the feedstream will comprise a mixture of butenes including isobutene and linear butenes, such as butene-1. There may also be present in the feedstream diolefin compounds, such as 1,3-butadiene. Because butene-1 and 1,3-butadiene are essentially non-reactive in the etherification reaction zone, such compounds will pass through the etherification reaction zone unreacted and with the first etherification reactor effluent. Since the etherification reaction is an equilibrium type reaction, the first etherification reactor effluent will also include the reactive isobutene and alcohol. Thus, the first etherification reactor effluent can include primary alcohol, such as methanol, tertiary olefin, such as isobutene, butene-1, 1,3-butadiene and an ether product of the etherification reaction.

The first etherification reactor effluent is passed as a feed to first separation means for separating the feed into a first stream containing ether among other etherification reaction products and a second stream containing the nonreactive compounds, such as butene-1 and 1,3-butadiene, isoolefins and alcohols charged to the first etherification reaction zone but which remained unconverted.

The second stream is contacted with an acidic ion exchange resin catalyst which is contained in a reactor vessel defining a second etherification reactor zone, under suitable etherification reaction conditions, to produce a second etherification reactor effluent stream. This second etherification section reactor effluent is then divided into two streams with at least a portion of the second etherification reactor effluent being fed to the first separation means whereby the ether product contained therein is separated from the nonreactive compounds, isoolefins and alcohols. The preferred embodiment of the invention includes passing at least a portion of the second etherification reactor effluent to the first separation means preferably as a feed and, most preferably, as a reflux. In this preferred embodiment of the invention, the remaining portion of the second etherification reactor effluent not charged to the first separation means is passed, or utilized as a feed, to a second separation means.

The second separation means provides for separating the remaining portion of the second etherification reactor effluent into a third stream, comprising ether, and a fourth stream comprising a primary alcohol, a tertiary olefin, butene-1 and 1,3-butadiene. The fourth stream is passed to a third etherification reactor zone defined by a reactor vessel and containing therein an acid ion exchange resin and in which primary alcohols and tertiary olefins of the fourth stream react to form ether contained in a third etherification reactor effluent stream. The third etherification reactor effluent comprises primary alcohols, butene-1, 1,3-butadiene, and a volumetric ratio of tertiary olefins to butene-1 of less than 0.2:100.

The third etherification reactor zone provides for the removal of the remaining isobutene of the fourth stream by reacting it with a primary alcohol by reacting it with a primary alcohol so as to provide the third etherification reactor effluent stream with a low enough concentration of isobutene to permit the subsequent preparation of a high purity butene-1 product having a volumetric ratio of isobutene to butene-1 of less than 0.2:100. Thus, the multiple etherification reaction steps remove from the original feedstream the reactive isobutene while allowing the non-reactive butene-1 to pass with the etherification reactor effluents having a reduced ratio of isobutene to butene-1. The removal of the isobutene by reactive means eliminates the need to use costly separation techniques to separate the butene isomers of isobutene and butene-1. It is preferred for the multiple etherification steps to convert a significant portion of the isobutene contained in the feedstream such that the volumetric ratio of isobutene to butene-1 in the third etherification reactor effluent is less than 0.15:100 and, most preferably, the ratio is 0.1:100. The third etherification reactor effluent may also contain primary alcohols, butene-1, and 1,3-butadiene.

The third etherification reactor effluent may be passed to an alcohol recovery system whereby the alcohol is separated and recovered for reuse from the ether, butene-1, 1,3-butadiene and other compounds contained in the third etherification reactor effluent.

The alcohol recovery system can be any suitable process system for separating solute components contained in solution, which in the present process is preferably a primary alcohol, from the remaining compounds of the solution, which are primarily hydrocarbons. Generally, it is preferred for the alcohol recovery system to be of the type involving conventional liquid-liquid extraction or solvent extraction methods wherein the third etherification reactor effluent is intimately contacted, by use of contacting means, with a solvent, such as water, to produce an extract stream containing the solvent rich in the alcohol solute and a raffinate stream. The raffinate stream is lean in alcohol content and is essentially the third etherification reactor effluent charged to the contacting means but having a substantial reduction in its alcohol content. The extract stream is passed to separation means, which is preferably a conventional fractionator, that provides an alcohol stream by separating the alcohol from the solvent.

The separated alcohol may be recycled and utilized as a reactant feed to the reaction section of the etherification process. The recovered solvent is recycled and reused in the contacting means for recovering alcohol from its feedstream. The raffinate stream, comprising butene-1 and 1,3-butadiene, is passed to a hydroisomerization zone defined by a reactor vessel containing a hydroisomerization catalyst wherein the diolefins, particularly 1,3-butadiene, are removed by a hydrogenation reaction to convert such diolefins to olefins and thereby forming a hydroisomerate stream having a reduced diolefin concentration.

The hydroisomerate stream, which has a low concentration of diolefins, such as 1,3-butadiene, and of isobutene, is passed to a separation system. The separation system provides means for separating the hydroisomerate stream into a high purity butene-1 stream, having a volumetric ratio of tertiary olefin to butene-1 of less than 0.2:100 and at least one other stream. The separation system may include any means which suitably provides for the separation and production of a high purity butene-1 product stream; however, an important aspect of the inventive process is the use of multiple etherification reaction zones in which the tertiary olefin of a feedstream containing a mixture of tertiary olefin and butene-1 are removed by use of an etherification reaction to convert such tertiary olefins to ether. By using this approach to removing tertiary olefins from a feedstream, the need to make the difficult separation between the butene isomers of isobutene and butene-1 is eliminated. Thus, the separation system preferably may include conventional fractionation means which are used to separate butene-1 from ether and the other compounds of the hydroisomerate stream. The fractionation of the hydroisomerate stream provides a high purity butene-1 that contains most of the isobutene of the hydroisomerate stream; but, due to the high conversion, multiple step etherification process, the high purity butene-1 product stream has a volumetric ratio of isobutene to butene-1 of less than 0.2:100.

The feedstream to the first etherification reaction zone of the process, as earlier described, is a mixed stream comprising a primary or a secondary alcohol, isoolefins and other compounds that are nonreactive in the presence of a acidic ion exchange resin catalyst at certain etherification reaction conditions. Generally, the isoolefins include those hydrocarbons having 4 to 16 carbon atoms per molecule. Examples of such isoolefins include isobutene, isoamylene, isohexylene, isoheptylene, isooctylene, isononylene, isodecylene, isoundecylene, isododecylene, isotridecylene, isotetradecylene, isopentadecylene, and isohexadecylene, or mixtures of two or more thereof. The preferred isoolefin is isobutene. The nonreactive compounds are linear olefins and diolefins. The preferred linear olefin is butene-1. While it is not generally desirable for the feedstream to contain a concentration of diolefin, the more common diolefin present is 1,3-butadiene.

The alcohols which may be charged or fed to the etherification reaction zones of the process include the primary and secondary aliphatic alcohols having from 1 to 12 carbon atoms, such as methanol, ethanol, propanol, isopropanol, the primary and secondary butanols, pentanols, hexanols, ethylene glycol, propylene glycol, butylene glycol, the polyglycols, and glycerol, etc., or mixtures of two or more thereof. The preferred alcohol is methanol.

It is generally preferred for the isoolefin and the alcohol to be passed through the etherification reaction zones of the process in the presence of diluents which do not have an adverse effect upon the etherification reaction and which are nonreactive under the conditions of etherification. Examples of suitable diluents include alkanes and straight chain olefins. The feed to the reactors, excluding alcohol, is generally diluted so as to include from about 2 to about 80 weight percent isoolefin, preferably from about 10 to about 60 weight percent. When it is desired to manufacture high purity butene-1, it should be present in the feedstream to the first etherification reaction zone at a concentration of no less than about 10 weight percent, preferably no less than 15 weight percent, most preferably, greater than 20 weight percent.

Any suitable molar ratio of alcohol to isoolefin in the feeds to the etherification reactor zones of the process can be utilized so as to give the desired high tertiary olefin conversion sought to be achieved by the process of this invention. Generally, the molar ratio of alcohol to isoolefin in the feeds to the etherification reaction zones of the process will be in the range of from about 0.5:1 to about 4:1; but, preferably, the molar ratio can range from about 0.8:1 to about 1.2:1. However, to achieve the highest conversion of the isoolefins in the process feeds to the etherification reaction zones, it is most preferable to have a molar ratio of alcohol to the isoolefin as close to 1:1 as is practically achievable. Charging the etherification reaction zone with a feed having a molar ratio of alcohol to isoolefin as close to 1:1 as is possible minimizes the production of unwanted byproducts, such as dimethyl ether, diethyl ether, tertiary butyl alcohol, and tertiary amyl alcohol.

Typically, etherification reactions are well known in the art and are not a critical aspect of this invention. The temperature for the etherification reaction zone and the space velocity for the feeds to the etherification reaction zones of the process can be selected as desired depending upon the degree of olefin conversion sought; but, generally, they should be such to provide the highest degree of olefin conversion that is economically feasible. Generally, the etherification reaction temperature will range upwardly to about 150° C. Preferably, the etherification reaction temperatures can range from about 30° C. to about 120° C, and most preferably, the temperature shall range from about 35° C. to about 80° C.

The operating pressure of the etherification reaction zones is generally selected to ensure that the feeds or charges to the reaction zones and the product streams from the reaction zones remain in the liquid phase during the etherification reaction. Typical pressures are in the range of from about 30 psig to about 300 psig. In most circumstances, the etherification reactions should be conducted in the liquid phase.

Generally, the liquid hourly space velocity (LHSV) of feed to the etherification reactors will be in the range of from about 1.0 hours$^{-1}$ to about 20 hours$^{-1}$; but, preferably, the LHSV can be in the range of from about 2 hours$^{-1}$ to about 10 hours$^{-1}$. Most preferably, the LHSV can be in the range of from 3 hours-$^{-1}$ to about 5 hours$^{-1}$.

The etherification reaction of the inventive process is that which selectively reacts tertiary olefins with alcohol, which can be either methanol or ethanol but is preferably methanol, to form a tertiary ether compound. The etherification reaction is an equilibrium type reaction that can be represented as follows:

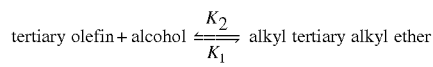

where $K_1$ and $K_2$ are rate constants.

Due to the values and temperature dependencies of the equilibrium constants of the aforementioned reaction, the equilibrium condition which favors the formation of the tertiary ether product is a low reactor temperature condition; but, in any event, because the etherification reaction is an equilibrium type reaction, the percent conversion of the tertiary olefin contained in a reaction zone to an ether product is thermodynamically limited. It has been surprisingly found that it is possible to increase tertiary olefin conversion by carrying out the etherification reaction process in multiple reaction stages with the second reaction stage following a separation step, which necessarily follows a first reaction stage, and with the second reaction stage being placed within the reflux loop of a fractionator that serves as the separation step. Accordingly, the entire overhead stream from the separation step following the first reaction stage will pass to the second reaction stage with at least a portion of the resultant second reaction stage effluent passing to such separation step as a reflux.

By utilizing the novel etherification process features and improvements, high tertiary olefin conversions can be achieved. For instance, in the case of an methyltertiarybutylether (MTBE) production mode process, the isobutene conversion across the process can exceed about 96 weight percent. Preferably, however, the isobutene conversion exceeds about 98 weight percent, and most preferably, the isobutene conversion can exceed 99 weight percent. When a high purity butene-1 product is being produced, a third additional etherification zone is required to convert the remaining isobutene so as to provide a third etherification reactor effluent having a volumetric ratio of tertiary olefin to butene-1 of less than 0.2:100.

The acid ion exchange catalysts utilized in the etherification reaction zones of the present invention are relatively high molecular weight carbonaceous material containing at least one SO$_3$H functional group. These catalyst are exemplified by the sulfonated coals ("ZeoKarb H", "Nalcite X" and "Nalcite AX") produced by the treatment of bituminous coals with sulfuric acid and commercially marketed as zeolitic water softeners or base exchangers. These materials are usually available in a neutralized form and in this case must be activated to the hydrogen form by treatment with a strong mineral acid such as hydrochloric acid and water washed to remove sodium and chloride ions prior to use. The sulfonated resin type catalysts are preferred for use in the present invention. These catalyst include the reaction products of phenolformaldehyde resins with sulfuric acid ("Amberlite IR-1", "Amberlite IR-100" and "Nalcite MX"). Also useful are the sulfonated resinous polymers of coumarone-indene with cyclopentadiene, sulfonated polymers of coumarone-indene with cyclopentadiene, and furfural and sulfonated polymers of cyclopentadiene with furfural. The most preferred cationic exchange resins are strongly acidic exchange resins consisting essentially of sulfonated polystyrene resin. These resins are manufactured and sold commercially under various trade names such as "Dowex 50", "Nalcite HCR" and "Amberlyst 15". As commercially obtained, they have solvent contents of about 50 percent and can be used as is or the solvent can be removed first. The resin particle size is not particularly critical and therefore is chosen in accordance with the manipulative advantages associated with any particular size. Generally mesh sizes of 10 to 50 U.S. Sieve Series are preferred. The reaction may be carried out in either a stirred slurry reactor or in a fixed bed continuous flow reactor. The catalyst concentration in a stirred slurry reactor should be sufficient to provide the desired catalytic effect. Generally catalyst concentration should be 0.5 to 50 percent (dry basis) by weight of the reactor contents with from 1 to 25 percent being the preferred range.

Acid ion exchange resins, such as Rohm & Haas Amberlyst 15 and Dow Chemical Dowex M-31, are currently the most preferred catalyst for the etherification.

The catalysts utilized in the hydroisomerization zone of this invention comprise the noble metals of Group VIII of the Periodic Table of Elements, as listed in the *Handbook of Chemistry and Physics,* published by the Chemical Rubber Company, in the 49th Edition (1969), page B-3. The catalysts intended to be included in the group of noble metals of Group VIII specifically are ruthenium, rhodium, palladium, osmium, iridium, and platinum.

Any of the usual catalyst supports can be employed, such as alumina (preferred), silica alumina, glass beads, and carbon. Catalysts in the form of pellets, spheres, and extrudates are satisfactory.

A preferred hydroisomerization catalyst is palladium on a carrier, the carrier preferably being alumina. The catalyst should contain from about 0.005 to about 2.0 percent palladium on alumina, preferably about 0.1 to about 1.0 weight percent palladium on alumina. Most preferably, the catalyst should contain from about 0.3 to about 0.5 weight percent palladium on alumina. A suitable catalyst weighs about 40 to about 60 pounds per cubic foot, has a surface area of about 30 to about 150 square meters per gram, a pore volume of about 0.35 to about 0.50 mL per gram, and a pore diameter of about 200 to about 500 Å.

As an example, a suitable commercial hydroisomerization catalyst satisfactory for use in this invention is manufactured by Mallinckrodt Specialty Chemicals Company, designated as Calsicat catalyst number E-144 SDU. The commercial catalyst contains about 0.55 weight percent palladium on alumina.

The hydroisomerization reaction is conducted at a reaction temperature of about 100° F. to about 300° F., preferably 130°–200° F.

The hydroisomerization process of this invention can be most effectively practiced at relatively low pressure conditions while maintaining the hydrocarbon most preferably in the liquid phase, although vapor phase operation can be used. Pressures employed for the liquid phase process are from about 100 to about 600 psig, preferably from about 150 to about 300 psig. Liquid hourly space velocities, LHSV, are maintained from about 2 to about 50, preferably from about 3 to about 10.

Hydrogen is utilized in the hydroisomerization zone by preferably being mixed with its feed prior to contacting the stream with the hydroisomerization catalyst. The hydrogen is necessary to effect double bond isomerization of the 1-olefin with the hydroisomerization catalysts and to provide for hydrogenation of diolefins to olefins. The hydrogen is added in amounts from 0.1 to 20.0 mol percent, preferably in amounts of about 1.0 to about 10.0 mol percent.

Now referring to FIG. 1, there is provided a schematic representation of the inventive process system 10 having a first etherification reactor 11, a second etherification reactor 12, a third etherification reactor 13, an alcohol recovery system 14, a hydroisomerization reactor 15, and a separation system 16.

An alcohol feedstream, which preferably contains methanol, is charged to process system 10 via conduit 18. A hydrocarbon feedstream, containing the reactive isoolefin of isobutene and a nonreactive diluent, such as butene-1, is charged via conduit 20 to process system 10. The two streams passing through conduits 18 and 20 are mixed together prior to passing by way of conduit 22 to first etherification reactor vessel 11, which defines a first etherification reaction zone wherein is contained an acidic ion exchange resin catalyst as described herein. The first etherification reaction zone is operated under suitable etherification reaction conditions so as to react at least a portion of the tertiary olefins with the alcohols contained in the feedstream to first etherification reactor reactor 11 to produce a first etherification reactor effluent.

The first etherification reactor effluent passes via conduit 26 to first separation means 28 which provides for the separation of its feeds into a first stream comprising the ether product produced from the reactions that take place in first etherification reactor 11 and a second stream containing unreacted alcohols, unreacted tertiary olefins and at least a substantial amount of the compounds contained in the incoming hydrocarbon feedstream that are nonreactive under the etherification reaction conditions at which first etherification reactor 11 operates.

First separation means 28 is any equipment or process which suitably can separate ether compounds from a stream comprising primary alcohols and hydrocarbon compounds, but it is preferred for first separation means 28 to be a conventional distillation column that defines a separation zone and which can comprise a rectifying zone and a stripping zone. In the novel process described herein, first separation means 28, or in the preferred case, first distillation column or first fractionator 28, will separate the first etherification reactor effluent into an overhead stream containing primary alcohols and hydrocarbons that passes as an overhead stream via conduit 30 to second etherification reactor 12 and a bottoms stream containing a first ether product that is conveyed from first separation means 28 via conduit 32.

Second etherification reactor 12 defines a second etherification reaction zone wherein is contained an acidic ion exchange resin catalyst identical to the type utilized in the first etherification reaction zone. Interposed in conduit 30 is heat exchanger 34 defining a heat transfer zone utilized for removing heat energy from the overhead stream leaving first separation means 28. The second etherification reactor effluent passes from second etherification reactor 12 via conduit 36. At least a portion of the second etherification reactor effluent passes by way of conduit 37 to first separation means 28. A remaining portion of the second etherification reactor effluent, after at least a portion of the second etherification reactor effluent is passed to first separation means 28, preferably as a feed, and most preferably as a reflux, is passed by way of conduit 38 to second separation means 40.

Second separation means 40 can be any suitable means for separating the remaining portion of said second etherification reactor effluent into a third stream comprising the ether product produced by the reaction of tertiary olefins with primary alcohols in second etherification reactor 12 and another stream comprising hydrocarbons, primary alcohols and any by-products produced in the previous two etherification reaction zones. It is preferable, however, for second separation means 40 to be a conventional distillation column or fractionator which defines a separation zone. In the use of the preferred distillation equipment, the bottoms product from second separation means 40 will comprise ether compounds produced in a second etherification reactor vessel 12 and passes from second separation means 40 by way of conduit 42.

The overhead stream from second separation means 40 comprises unreacted hydrocarbons, primary alcohols and undesirable reaction by-products that pass by way of conduit 44 to third etherification reactor 13. Interposed in conduit 44 is heat exchanger 46 defining a heat transfer zone utilized for removing heat energy from the overhead stream leaving second separation means 40.

Third etherification reactor 13 defines third etherification zone wherein is contained an acidic ion exchange resin catalyst identical to the type used in the first etherification reactor 11 and second etherification reactor 12. A third etherification reactor effluent passes from third etherification reactor 13 through conduit 48 and is charged to alcohol recovery system 14 whereby the alcohol compounds are separated from the unreacted hydrocarbons and other undesirable reaction by-products such as dimethylether.

Within alcohol recovery system 14 is contacting means 50 for contacting an extraction solvent or solvent with the third etherification effluent charged to contacting means 50 by way of conduit 48. Contacting means 50 can be any suitable piece of equipment for contacting a solvent with a feed solution containing a solute, which in the instant case is alcohol, and preferably, contacting means 50 will be a contacting vessel defining a contacting zone and equipped with either trays or packing for assisting in the intimate contacting of the solution and solvent. Contacting means 50 produces a raffinate stream, which is substantially free of alcohol, and an extract stream comprising a solvent rich in alcohols. The raffinate stream is removed as an overhead stream from contacting means 50 and passes by way of conduit 52 to hydroisomerization reactor 15.

The extract stream from contacting means 50 is a solvent utilized for recovering the primary alcohols from the feedstream charged to contacting means 50 which is rich in primary alcohols. The extract stream, comprising the solvent rich in primary alcohols, passes by way of conduit 60 to separating means 62 for separating the extract solvent rich in primary alcohols into an alcohol stream and a stream of recovered solvent lean in primary alcohols. Separating means 62 can be any equipment suitable for separating the primary alcohols from the solvent that is charged to it and will preferably be a conventional distillation column or fractionator defining a separation zone. The overhead from separating means 62 is the separated alcohol and passes from separating means 62 by way of conduit 64. The recovered solvent, which is lean in primary alcohols, is recycled back to contacting means 50 by way of conduit 66 and is utilized as the solvent for contacting means 50.

Hydroisomerization reactor 15 defines a hydroisomerization reaction zone wherein is contained a hydroisomerization catalyst. Hydroisomerization reactor 15 hydrogenates the diolefin contained in the raffinate stream charged thereto and provides a hydroisomerate stream that is relatively free of diolefins. Makeup hydrogen through is provided through conduit 67 for the hydroisomerization reaction. The hydroisomerate stream passes from hydroisomerization reactor 15 through conduit 68 and is charged to separation system 16. Separation system 16 defines a separation zone and provides means for separating the hydroisomerate stream into a high purity butene-1 product stream, which passes from separation system 16 by way of conduit 69, and at least one other stream. The streams, other than the high purity butene-1 product stream, may include a light ends stream containing dimethylether, an alkylation process feedstream, and a heavy ends stream, each respectively passing from separation system 16 by way of conduits 70, 72 and 74.

Calculated

EXAMPLE I

To illustrate the inventive process shown in FIG. 1, this calculated example is provided. The material balance for the calculated example is presented in Table I. The stream numbers shown in Table I correspond to those represented in FIG. 1. As can be seen from the material balance, essentially all the isobutane of the hydrocarbon feed stream is consumed in the etherification reaction to produce MTBE while the remaining hydrocarbons of the hydrocarbon feed stream pass through the process system as various products. Essentially all the 1,3-butadiene of the hydrocarbon feedstream is removed by the hydroisomerization step. Approximately half of the 1-butene and 2-butene passes with a product stream that may suitably be used as an alkylation process feed.

TABLE I

Material Balance

| Stream No. | 20 HC Feed | 18 MeOH | 32 + 42 MTBE | 67 H2 | 69 1C4= | 70 DME | 72 Alky Feed | 74 Heavies |
|---|---|---|---|---|---|---|---|---|
| H2 | | | | 5.09 | | 0.57 | | |
| C1 | | | | 0.73 | | 0.73 | | |
| C2 | | | | 1.36 | | 1.36 | | |
| C3 | 105.94 | | | | | 89.99 | 16.42 | |
| C3= | 122.98 | | | | | 118.99 | 6.25 | |
| iC4 | 2633.1 | | 0.11 | | 4.94 | 130.91 | 2496.76 | |
| nC4 | 1475 | | 0.14 | | 1.4 | 11.72 | 1454.76 | 6.63 |
| 1C4= | 3640.8 | | 0.11 | | 1859.12 | 86.15 | 1506.05 | 0.22 |
| c-2-C4= | 2035.9 | | 0.19 | | | 8.56 | 2032.49 | 30.02 |
| t-2-C4= | 2943.4 | | 0.18 | | 0.42 | 25.25 | 3064.35 | 16.59 |
| iC4= | 6521.3 | | 0.01 | | 0.95 | 0.1 | | 2.51 |
| iC5 | 345.29 | | 16.45 | | | 0.01 | 51 | 277.83 |
| 1,3-butadiene | 12.99 | | | | 0.05 | | | |
| Propadiene | 2.6 | | | | | | | |
| MTBE | | | 10133.15 | | | | 0.03 | 56.25 |
| TBA | | | 30.15 | | | | 0.09 | 0.37 |
| DIB | | | 6.36 | | | | | |
| DME | | | | | | 2.37 | 1.19 | |
| H2O | | 1.05 | | | | 4.3 | | |
| MeOH | | 3710.52 | 0.01 | | | 0.05 | 0.02 | |
| kg/hr | 19839.3 | 3711.57 | 10186.86 | 7.18 | 1866.88 | 481.06 | 10631.92 | 387.91 |

Reasonable variations and modifications are possible within the scope of the foregoing disclosure, drawings and appended claims.

That which is claimed is:

1. A process comprising:
    passing from a first etherification reactor zone a first etherification reactor effluent containing primary alcohols, tertiary olefins, butene-1, 1,3-butadiene and ether to first separation means for separating feeds into a first stream, comprising ether, and a second stream, comprising primary alcohols, tertiary olefins, butene 1 and 1,3-butadiene;
    passing said second stream to a second reactor zone containing therein an acidic ion exchange resin and wherein the primary alcohols and tertiary olefins of said second stream react to form ether which is contained in a second etherification reactor effluent stream;
    passing a portion of said second etherification reactor effluent stream to said first separation means;
    passing the remaining portion of said second etherification effluent stream to second separation means for separating the remaining portion of said second etherification reactor effluent stream into a third stream, comprising ether, and a fourth stream, comprising primary alcohols, tertiary olefins, butene-1 and 1,3-butadiene; and passing said fourth stream to a third reactor zone containing therein said acidic ion exchange resin and wherein primary alcohols and tertiary olefins of said fourth stream react to form ether which is contained in a third etherification reactor effluent stream wherein said third etherification reactor effluent stream contains primary alcohols, butene-1, 1,3-butadiene and a volumetric ratio of tertiary olefins to butene-1 of less than 0.2:100.

2. A process as recited in claim 1, further comprising:

passing said third etherification reactor effluent stream to an alcohol recovery system whereby primary alcohols are recovered from said third etherification reactor effluent stream to produce an alcohol stream comprising a primary alcohol, and a raffinate stream, comprising butene-1 and 1,3-butadiene.

3. A process as recited in claim 2, further comprising:

hydroisomerizing said raffinate stream to thereby remove the 1,3-butadiene from said extract stream and providing a hydroisomerate stream.

4. A process as recited in claim 3, further comprising:

passing said hydroisomerate stream to separation system means for separating said hydroisomerate stream into a high purity butene-1 stream having a volumetric ratio of tertiary olefin to butene-1 of less than 0.2:100 and at least one other stream.

* * * * *